(12) United States Patent
Messinger

(10) Patent No.: US 11,249,074 B1
(45) Date of Patent: Feb. 15, 2022

(54) REUSABLE DIAGNOSTIC MEDICAL TESTER

(71) Applicant: Samuel Messinger, Ramot Beit Shemesh Gimmel (IL)

(72) Inventor: Samuel Messinger, Ramot Beit Shemesh Gimmel (IL)

(*) Notice: Subject to any disclaimer, the term of this patent is extended or adjusted under 35 U.S.C. 154(b) by 0 days.

(21) Appl. No.: 17/400,389

(22) Filed: Aug. 12, 2021

(51) Int. Cl.
*G01N 33/53* (2006.01)
*H01M 8/16* (2006.01)

(52) U.S. Cl.
CPC .......... *G01N 33/5302* (2013.01); *H01M 8/16* (2013.01); *H01M 2250/30* (2013.01)

(58) Field of Classification Search
CPC . G01N 33/5302; H01M 8/16; H01M 2250/30
See application file for complete search history.

(56) References Cited

U.S. PATENT DOCUMENTS

| 9,723,433 | B2 | 8/2017 | Sorin |
| 10,340,546 | B1 | 7/2019 | Messinger |

*Primary Examiner* — Sarah A. Slifka

(57) ABSTRACT

A multi-use testing device is disclosed that is able to test a user fluid or dissolved tissue samples for a medical condition comprising, e.g.: blood related, heart (FABS enzymes); liver and kidney function; gene mutations; COVID-19; and pregnancy status. The testing device is positioned in a bio-fluid chamber configured to store at least one electrolyte or charging fluid to create a conductive path for electrons emitted by an anode electrode and a cathode electrode to generate electricity to recharge the micro battery. The generated electricity is transferred to power the testing device. The reusable testing device further comprises a computing device configured to control the communication between a user electronic computing device and the testing device. The reusable testing device is dipped into a sample in a container and outputs the encrypted test result for wireless transmission to electronic computing devices.

20 Claims, 2 Drawing Sheets

REUSABLE DIAGNOSTIC MEDICAL TESTER

BACKGROUND OF THE INVENTION

A. Technical Field

The present invention generally relates to medical devices, e.g. over-the-counter. More particularly, the present invention relates to a reusable testing device configured to provide easy, reliable, and reusable testing procedure, thereby allowing a user to conduct an at home diagnostic medical test repeatedly without having to buy a new test kit, e.g. an at home pregnancy test, COVID-19, etc.

B. Description of Related Art

The development of medical devices has dramatically increased in the field of medicine. Medical devices benefit patients by helping health care providers diagnose and treat patients and helping patients overcome sickness or disease, improving their quality of life. Over the last decade, the use of stents, drug eluting stents, pacemakers, defibrillators, ventricular assist devices, glucose infusion pumps and neurostimulators has increased many folds. Some of the above enumerated examples, as well as a number of other implantable and/or non-implantable medical devices, are active devices that require power sources for operation.

The conventional power sources or batteries that are utilized in conjunction with implantable or non-implantable medical devices typically have stringent specifications imposed upon them relative to their physical size and performance. In older generation power sources, batteries that were designed for implantable medical devices were larger batteries, as compared to today's miniature batteries, and with a relatively short useful life.

Currently, a bio-battery is an energy storing device that is powered by organic compounds, usually being glucose, such as the glucose in human blood. When enzymes in human bodies break down glucose, several electrons and protons are released. Therefore, by using enzymes to break down glucose, bio-batteries directly receive energy from glucose. These batteries then store this energy for later use. Such bio-batteries are rechargeable fuel batteries that use electrodes in liquid form. This type of battery can either be recharged or the liquid electrodes can be replaced.

In addition, such bio-fueling batteries are used in several medical devices, thereby making them compact and portable so that a user can buy it for at home testing. However, with the advent of miniature implantable medical devices for such diverse applications as drug delivery, glucose sensing and monitoring, and neurostimulation, batteries are required that are capable of providing useful power and occupying ever smaller volumes. Further, the medical devices, e.g. pregnancy testers, used in the home are expensive and could be used only once.

The U.S. Pat. No. 10,340,546 B 1 entitled "Self-rechargeable bio-fueling micro battery with a glucose burning chamber" (the entirety of which is hereby incorporated in by reference), discloses various embodiments of a biocompatible, self-rechargeable bio-fueling micro battery with a glucose burning chamber to power an implanted medical device. The micro battery comprises a bio-membrane that is configured to diffuse a plurality of bio-fluids across an anode and cathode electrode. The bio-membrane includes: a biocompatible compartment storing at least one of a chemical substance configured to operate a plurality of bio-medical implant devices; one or more bio-fuel compartments or cells (blood, glucose, and/or microbial) configured to store bio-fuels for generating electrolyte and to create a conductive path for electrons emitted by electrodes; and a processor in communication with the biocompatible compartment through plurality of connectors interface with the one or more bio fuel compartments to control the communication between user and the bio medical implant devices. The biofluids comprise a lemon juice, an orange juice, a pineapple juice, and a sour juice; and/or an ingested food.

Therefore, there is a need for an implantable, self-rechargeable, bio-fueling micro battery that is usable for powering medical devices. Also, there is a need for a pregnancy testing device to provide easy, reliable, and reusable pregnancy testing procedure, thereby allowing a user/woman to conduct the pregnancy test in a home by themself.

SUMMARY OF THE INVENTION

The present invention generally discloses medical devices. Further, the present invention discloses a reusable testing device configured to provide easy, reliable, and reusable pregnancy testing procedure, thereby allowing a user/woman to conduct the pregnancy test in a home by themself.

In one embodiment, the reusable testing device is an innovating and intelligent multi-use pregnancy tester designed to detect the pregnancy of a women being tested in a home. In one embodiment, the reusable testing device is a rechargeable and reusable pregnancy tester. The reusable testing device is configured to provide easy, reliable, and reusable pregnancy testing procedure, thereby allowing the user/woman to conduct the pregnancy test in a home by themself. In one embodiment, the reusable testing device has a self-rechargeable bio-fueling micro battery. In one embodiment, the micro battery is positioned in the bio-fluid chamber. In one embodiment, bio-fluid chamber is configured to store at least one electrolyte or charging fluid to recharge the micro battery.

In one embodiment, the reusable testing device is kept in the bio-fluid chamber to charge the micro battery. In one embodiment, the bio-fluid chamber is filled with the electrolyte. In one embodiment, the electrolyte is configured to create a conductive path for electrons emitted by an anode electrode and a cathode electrode to generate electricity to recharge the micro battery. In one embodiment, the generated electricity is transferred to power the reusable testing device. In some embodiments, the electrolyte could be, but not limited to, lemon juice, orange juice, pineapple juice, and sour juice. In an exemplary embodiment, the electrolyte is lemon juice.

In one embodiment, the reusable testing device comprises a main body having an upper end and a lower end. In one embodiment, the upper end has a handle for holding and easy handling of the reusable testing device. In one embodiment, the main body encloses a self-rechargeable bio-fueling micro battery. The micro battery has a bio-membrane configured to diffuse at least one bio-fluid to generate electron flow for recharging the micro battery and supplying a constant power supply to the reusable testing device.

In one embodiment, the reusable testing device further comprises a computing device. In one embodiment, the computing device comprises a processor and a memory in communication with the processor configured to store a set of instructions executable by the processor. In one embodiment, the computing device is configured to control the communication between a user electronic computing device and the reusable testing device. In an exemplary embodiment, the reusable testing device is configured to test the pregnancy by the user in the home by themself. In one embodiment, the reusable testing device is dipped into the sample in a container and outputs the test result, which may be read from a display window on the test device (e.g. end of handle or on main body), and/or which may be wirelessly transmitted for reading on a user electronic computing device.

In one embodiment, the reusable testing device outputs the pregnancy test result.

In another embodiment, the reusable testing device outputs blood glucose levels.

In one embodiment, the user electronic computing device could be, but not limited to, a computer, a laptop, a smartphone, a remote device, a personal digital assistant (PDA), a mobile phone, and a tablet, with a mobile application of the present invention installed thereon, or a website accessible via the network In one embodiment, the computing device is kept in the electrolyte to recharge the micro battery. In some embodiments, the electrolyte is any one of lemon juice, orange juice, pineapple juice, and sour juice. The generated electricity is then transferred from the micro battery to the reusable testing device, thereby powering the reusable testing device without the need for any additional or external power source. The reusable testing device is dipped into the sample being tested. In one embodiment, the sample is the user's urine. In one embodiment, the reusable testing device could be wirelessly updated for testing other diseases found in the sample. In one embodiment, the reusable testing device is reprogrammed as needed to detect other diseases including, but not limited to, heart attack FABS enzyme testing, coronavirus, and malaria.

In one embodiment, a method of using the reusable testing device comprises the following steps. At one step, a self-rechargeable bio-fueling micro battery is provided. In one embodiment, the micro battery has a bio-membrane configured to diffuse at least one bio-fluid to generate electron flow for recharging the micro battery and supplying a constant power supply to the reusable testing device. At another step, the electrolyte or charging fluid is injected to create a conductive path for electrons emitted by an anode electrode and a cathode electrode to generate electricity to recharge the micro battery. In one embodiment, the electrolyte is any one of lemon juice, orange juice, pineapple juice, and sour juice. In an exemplary embodiment, the electrolyte is lemon juice.

At another step, electricity is generated by one or more bio-fuel cells to recharge the micro battery. In one embodiment, the generated electricity is transferred from the micro battery to the reusable testing device, thereby powering the reusable testing device without the need for any additional or external power source. At another step, the reusable testing device is dipped into a sample of a user being tested to output the test result. In one embodiment, the reusable testing device outputs the pregnancy test result. In one embodiment, the reusable testing device is wirelessly updated for testing other diseases found via the sample. In one embodiment, the reusable testing device further could be reprogrammed to detect other diseases including, but not limited to, heart attack, coronavirus, and malaria.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1:
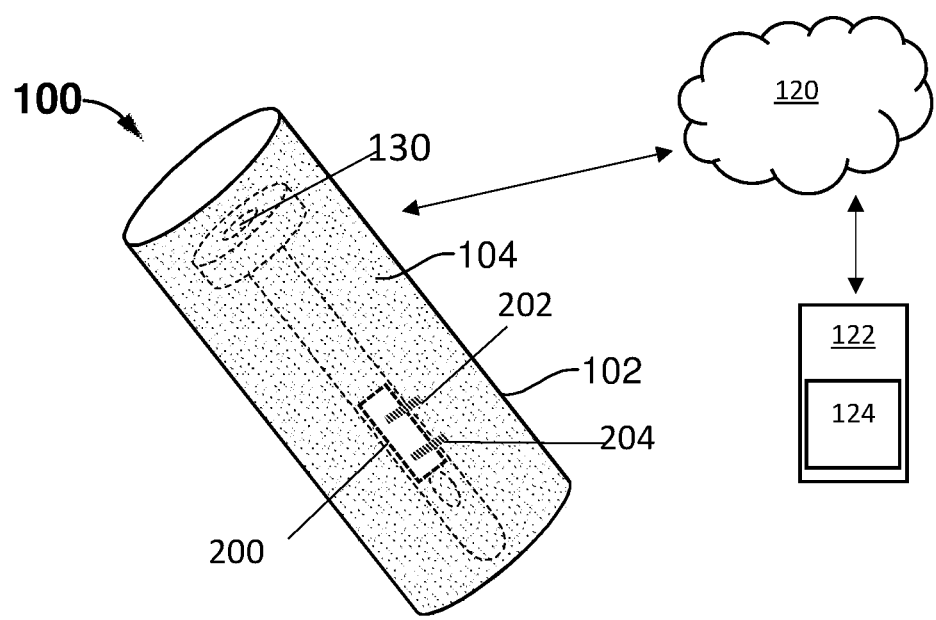
FIG. 1 shows a multi-use testing device kept in a bio-fluid chamber in an embodiment of the present invention.

Referring to FIG. 1, a multi-use testing device 100 kept in a bio-fluid chamber 102, according to one embodiment of the present invention. In one embodiment, the reusable testing device 100 is an innovating and intelligent pregnancy tester designed to detect the pregnancy of a women being tested in a home. In an exemplary embodiment, the reusable testing device 100 is a rechargeable and reusable pregnancy tester. The reusable testing device 100 is configured to provide easy, reliable, and reusable pregnancy testing procedure, thereby allowing a user/woman to conduct the pregnancy test in a home by themself. In one embodiment, the reusable testing device 100 has a self-rechargeable bio-fueling micro battery. In one embodiment, the micro battery is positioned in the bio-fluid chamber 102. In one embodiment, bio-fluid chamber 102 is configured to store at least one electrolyte or charging fluid 104 to recharge the micro battery.

In one embodiment, the reusable testing device 100 is kept in the bio-fluid chamber 102 to charge the micro battery. In one embodiment, the bio-fluid chamber 102 is filled with the electrolyte 104. In one embodiment, the electrolyte 104 is configured to create a conductive path for electrons emitted by an anode electrode and a cathode electrode to generate electricity to recharge the micro battery. In one embodiment, the generated electricity is transferred to power the reusable testing device 100. In some embodiments, the electrolyte 104 could be, but not limited to, lemon juice, orange juice, pineapple juice, and sour juice. In an exemplary embodiment, the electrolyte 104 is lemon juice.

Figure 2:
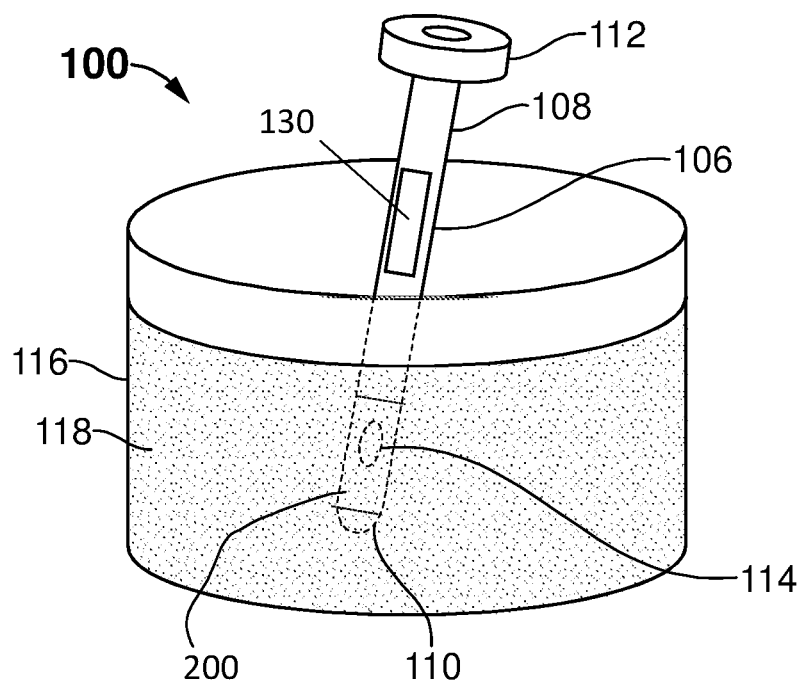
FIG. 2 shows the reusable testing device dipped in a sample of a user being tested in one embodiment of the present invention.

Referring to FIG. 2, the reusable testing device 100 dipped in a sample 118 of a user being tested, according to one embodiment of the present invention. In one embodiment, the reusable testing device 100 comprises a main body 106 having an upper end 108 and a lower end 110. In one embodiment, the upper end 108 has a handle 112 for holding and easy handling of the reusable testing device 100. In one embodiment, the main body 106 encloses a self-rechargeable bio-fueling micro battery. The micro battery has a bio-membrane configured to diffuse at least one bio-fluid to generate electron flow for recharging the micro battery and supplying a constant power supply to the reusable testing device 100.

Figure 3:
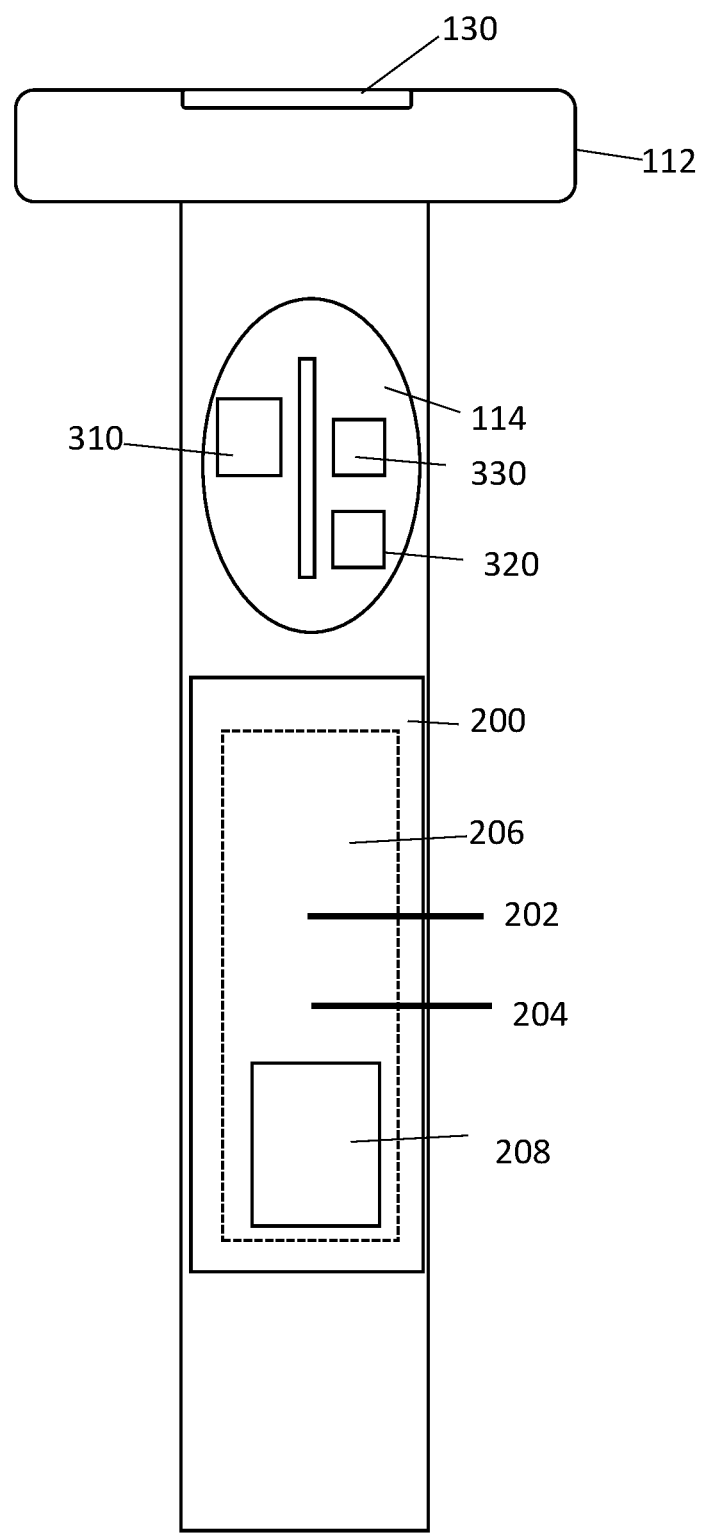
FIG. 3 is an exemplary embodiment of the testing device comprising a micro-battery with a computing device housed within the micro-battery.

In one embodiment, the reusable testing device 100 further comprises a computing device 114. In one embodiment, as illustrated in FIG. 3, the computing device 114 comprises a micro-processor 310 and a memory 320 in communication with the processor configured to store a set of instructions executable by the processor. The memory could include computer storage media in the form of volatile and/or nonvolatile memory such as read only memory (ROM) and/or random-access memory (RAM). In one embodiment, the computing device 114 is a chip with a computer. In one embodiment, the computing device 114 is wirelessly connected to the external device or communication source via a network 120. In one embodiment, the network is at least any one of, but not limited to, Wi-Fi, Bluetooth wireless local area network (WLAN), and a radio communication network.

The wireless transmissions from the testing device may also be encrypted, such as per the methods disclosed in U.S. Pat. No. 9,723,433 B2 that issued on Aug. 1, 2017 and is entitled "Systems and methods for wireless communication with implantable and body worn devices" (e.g. see FIG. 4). The entirety of this reference is incorporated herein. In an embodiment, wireless transmissions (e.g. text messages, instant messages, emails, etc.) are sent from the reusable testing device 100 to the user's electronic computing device (e.g. smartphone) and concurrently or alternatively to a user's medical professional (e.g. their doctor's office computer).

In one embodiment, the computing device 114 is configured to control the communication between a user electronic computing device and the reusable testing device 100. In one embodiment, the reusable testing device 100 is dipped into the sample 118 in a container 116 and outputs the test result. In one embodiment, the user electronic computing 122 device could be, but not limited to, a computer, a laptop, a smartphone, a remote device, a personal digital assistant (PDA), a mobile phone, and a tablet.

User electronic computing 122 device may further comprise a mobile application 124 of the present invention for interpreting and displaying test results, and may further comprise instructions on how to use the test device. The mobile application comprises one or more non-transitory computer-readable storage media having computer-executable instructions stored thereon which, when executed by one or more user electronic computing devices, cause it to perform operations to, e.g. receive and display data.

In one embodiment, the computing device 114 is kept in the electrolyte 104 as shown in FIG. 1 to recharge the micro battery. In some embodiments, the electrolyte 104 is any one of lemon juice, orange juice, pineapple juice, and sour juice. The generated electricity is then transferred from the micro battery to the reusable testing device 100, thereby powering the reusable testing device 100 without the need for any additional or external power source. The reusable testing device 100 is dipped into the sample 118 being tested. In one embodiment, the sample 118 is user's urine. In one embodiment, the reusable testing device 100 could be wirelessly updated for testing other diseases found in the sample 118. In one embodiment, the reusable testing device 100 outputs the pregnancy test result. In one embodiment, the reusable testing device 100 is reprogrammed as needed to detect other diseases including, but not limited to, heart attack, coronavirus, cancer, and malaria.

In one embodiment, a method of using the reusable testing device 100 comprises the following steps. At one step, a self-rechargeable bio-fueling micro battery is provided. In one embodiment, the micro battery has a bio-membrane (see FIG. 3, 206) configured to diffuse at least one bio-fluid to generate electron flow for recharging the micro battery and supplying a constant power supply to the reusable testing device 100. At another step, the electrolyte or charging fluid 104 is injected into the device 100 to create a conductive path for electrons emitted by an anode electrode 202 and a cathode electrode 204 to generate electricity to recharge the micro battery. In one embodiment, the electrolyte 104 is any one of lemon juice, orange juice, pineapple juice, and sour juice. In an exemplary embodiment, the electrolyte 104 is lemon juice.

At another step, electricity is generated by one or more bio-fuel cells to recharge the micro battery. In one embodiment, the generated electricity is transferred from the micro battery to the reusable testing device 100, thereby powering the reusable testing device 100 without the need for any additional or external power source. At another step, the reusable testing device 100 is dipped into a sample 118 of a user being tested to output the test result. In an exemplary embodiment, the reusable testing device is configured to test pregnancy by the user in the home by themself. In one embodiment, the reusable testing device 100 is wirelessly updated for testing other diseases found via the sample 118. In one embodiment, the reusable testing device 100 further could be reprogrammed to detect other diseases including, but not limited to, heart attack, coronavirus, cancer, and malaria.

In one embodiment, the reusable testing device 100 is used to detect malaria from a sample collected from the user. The sample could contain malaria *Plasmodium falciparum* hrpz, which is a poly-histidine antigen. In one embodiment, the poly-hisdine is rich in protein-2. In one embodiment, the reusable testing device 100 could also be used to conduct urine test for coronary disease, where the protein expressions or biomarkers provide about 90% accurate coronary test result. In one embodiment, the reusable testing device 100 could be used to detect thyroid tumor markers level and liver fibrosis. In one embodiment, the reusable testing device 100 could be a prostrate cancer test kit. In some embodiments, the reusable testing device 100 could also be used to conduct cancer test such as breast cancer urine test, PSA (Prostate-Specific Antigen) urine test, prostrate urine risk (PUR) test, and prostrate urine test. In some embodiments, the reusable testing device 100 could be used for urine test such as malaria urine test, cancer urine test, heart attack urine test, and other urine test for other diseases.

Advantageously, the reusable testing device provides easy, reliable, and reusable pregnancy testing procedure. The reusable testing device provides allows women to test the pregnancy in a home by themself. The pregnancy testing procedure is easy and inexpensive. The reusable testing device is rechargeable and reusable. The reusable testing device could be recharged using the self-rechargeable bio-fueling micro battery without the need of additional or external power source. Further, the reusable testing device could be reprogrammed to detect other viruses and diseases such as heart attack, coronavirus, cancer, and malaria.

Micro-Battery Vs Generator

In an embodiment, the reusable testing device is powered by a hand cranked mini generator well known in the art. In another embodiment, a micro-battery within or attached to the reusable testing device is used, such as a standard replaceable or recharged micro-battery well known in the art. In a preferred embodiment, a micro-battery using a bio-fuel as disclosed herein is used.

FIGS. 1 and 3 illustrates an exemplary embodiment where in the computing device 114 is separate from the micro-battery 200, but attached to it to transmit data between the two. In this embodiment, the micro-battery does not require its own micro-processor, memory, wireless transmitter, etc. Computing device 114 can be located a variety of places on the main body 106. For example, in FIGS. 1 and 2 device 114 is positioned near the lower end. And in FIG. 3, it is positioned between and connected to both a display window 130 for showing test results, and the micro-battery 200.

FIG. 2 illustrates another embodiment wherein the computing device 114 is within the micro-battery 200. For example, the U.S. Pat. No. 10,340,546 B1 discloses a micro-battery with a processor and memory housed within it. In another embodiment (not shown), the testing device 100 can have both a micro-battery processor and memory connected to the computing device 114.

As further illustrated in FIG. 3, micro-battery 200 comprises a bio-membrane 206 is configured to diffuse at least one bio-fluid or electrolyte (FIG. 1, 104 across the anode electrode 202 and the cathode 204 electrode to generate electron follow for recharging the micro battery and/or for supplying power to the testing device 100).

In the embodiment shown in FIGS. 1 and 3, the anode and cathode electrode extend outside the testing device 100 and into the electrolyte 104 to recharge the micro-battery while it is still in the biofluid chamber 102. In another embodiment (not shown), the anode and cathode electrodes do not extend outside of the bio-membrane 206, and the electrolyte must diffuse through it to contact the electrodes.

As illustrated in FIG. 3, the micro-battery may further comprise one or more bio-fuel cells as disclosed in U.S. Pat. No. 10,340,546 B1.

Once the micro-battery is fully charged, the user removes the stick-main body 116 from the biofluid chamber 102 and inserts it into the container 116 which stores a user's bodily sample (e.g. urine, blood, saliva, etc.) to make contact with the computing device 114 to analyze and display the test results (either on the stick at 130, or via wirelessly transmitting to a user electronic computing device via a wireless network).

Methods of computing test results are well known in the art specific to each test type. For example, in a pregnancy test, the main body 106 further comprises test strips able to detect the presence of pregnancy hormone human chorionic gonadotrophin (hCG). And in blood glucose tests, the main body components for generating electrical current through a blood sample to read the level of resistance. And for cancer and infectious diseases, the main body further comprises components for detecting antibodies specific to the disease.

Preferred embodiments of this invention are described herein, including the best mode known to the inventors for carrying out the invention. It should be understood that the illustrated embodiments are exemplary only and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A multi-use testing device, comprising:
    a main body having an upper end and a lower end, wherein the main body encloses a self-rechargeable bio-fueling micro battery having at least one biofuel cell, and a bio-membrane configured to diffuse at least one bio-fluid to generate electron flow for recharging the micro battery and supplying a constant power supply to the testing device;
    a bio-fluid chamber configured to store at least one electrolyte or charging fluid to create a conductive path for electrons emitted by an anode electrode and a cathode electrode to generate electricity to recharge the micro battery, wherein the generated electricity is transferred to power the testing device, and
    a computing device configured to control the communication between a user electronic computing device and the testing device, wherein the testing device is dipped into a sample in a container and outputs the test result.

2. The testing device of claim 1, is a reusable pregnancy tester.

3. The testing device of claim 1, wherein the computing device comprises a processor and a memory in communication with the processor configured to store a set of instructions executable by the processor.

4. The testing device of claim 1, wherein the computing device is kept in the electrolyte to recharge the micro battery.

5. The testing device of claim 1, wherein the electrolyte is any one of lemon juice, orange juice, pineapple juice, and sour juice.

6. The testing device of claim 1, wherein the lower end of the testing device is dipped into the sample being tested.

7. The testing device of claim 1, wherein the sample is user's urine.

8. The testing device of claim 1, is wirelessly updated for testing one or more diseases found in the sample.

9. The testing device of claim 3, wherein the computing device processor stores instructions for testing for one or more diseases comprising: heart attack, bacterial or viral infections, coronavirus, cancer, and malaria.

10. The testing device of claim 9, wherein the coronavirus is COVID-19.

11. The testing device of claim 1, wherein the biofuel cells are able to generate and/or store electricity by one or more biofuel cells to recharge the micro battery, and transfers the generated electricity from the micro battery to power the testing device.

12. A method of using a multi-use testing device, comprising the steps of:
    a) providing a testing device comprising:

i) a main body having an upper end and a lower end, wherein the main body encloses a self-rechargeable bio-fueling micro battery having at least one bio-fuel cell and a bio-membrane configured to diffuse at least one bio-fluid to generate electron flow for recharging the micro battery and supplying a constant power supply to the reusable testing device;

ii) a bio-fluid chamber configured to store at least one electrolyte or charging fluid to create a conductive path for electrons emitted by an anode electrode and a cathode electrode to generate electricity to recharge the micro battery, wherein the generated electricity is transferred to power the testing device;

iii) a computing device configured to control the communication between a user electronic computing device and the testing device, wherein the testing device is dipped into a sample in a container and outputs the test result;

b) injecting or diffusing an electrolyte or charging fluid to create a conductive path for electrons emitted by the anode electrode and the cathode electrode to generate electricity to recharge the micro battery and/or to power the testing device;

c) generating and/or storing electricity by one or more bio-fuel cells to recharge the micro battery, and transferring the generated electricity from the micro battery to power the testing device, and d) placing the testing device into a sample of a user being tested to analyze and output the test result.

13. The method of claim 12, wherein the sample comprises a user's urine, blood, and/or saliva.

14. The method of claim 12, wherein the sample is any user body fluid or tissue comprising a user's genetic material for use in a genetic test.

15. The method of claim 12, wherein the electrolyte is any one of lemon juice, orange juice, pineapple juice, and sour juice.

16. The method of claim 12, wherein the reusable testing device is wirelessly updated for testing one or more diseases found in the sample.

17. The method of claim 12, wherein the computing device processors stores instructions for testing for one or more diseases comprising: heart attack, bacterial and viral infections, coronavirus, cancer, and malaria.

18. The testing device of claim 17, wherein the coronavirus is COVID-19.

19. The method of claim 12, wherein the computing device analyzes and displays the test results on the testing device, or wirelessly transmits data to a user electronic computing device.

20. The method of claim 19, wherein the test result is encrypted for wireless transmission to the user's electronic computing device and to a doctor's electronic computing device.

* * * * *